(12) United States Patent
Blake et al.

(10) Patent No.: US 12,042,212 B2
(45) Date of Patent: Jul. 23, 2024

(54) FLOW VALVE POSITION SENSOR FOR AN ELECTROSURGICAL DEVICE

(71) Applicant: GYRUS MEDICAL LIMITED, Cardiff (GB)

(72) Inventors: Nathan Philip Blake, Cardiff (GB); Rhydian Hoddinott, Cardiff (GB); Ben Clarke, Cardiff (GB); Liam John McAleer, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 110 days.

(21) Appl. No.: 17/370,602

(22) Filed: Jul. 8, 2021

(65) Prior Publication Data
US 2022/0031381 A1 Feb. 3, 2022

(30) Foreign Application Priority Data
Aug. 3, 2020 (GB) ...................................... 2012025

(51) Int. Cl.
*A61B 18/00* (2006.01)
*A61B 18/14* (2006.01)

(52) U.S. Cl.
CPC .. *A61B 18/148* (2013.01); *A61B 2018/00577* (2013.01); *A61B 2018/00589* (2013.01);
(Continued)

(58) Field of Classification Search
None
See application file for complete search history.

(56) References Cited

U.S. PATENT DOCUMENTS 6,096,068 A * 8/2000 Dobak, III ................ A61F 7/12
607/105
6,689,146 B1 2/2004 Himes
(Continued)

FOREIGN PATENT DOCUMENTS

AU 2012241135 B2 11/2012
JP 2005-245722 A 9/2005
(Continued)

OTHER PUBLICATIONS

Annotated Himes Fig 1 (Year: 2023).*
(Continued)

*Primary Examiner* — Linda C Dvorak
*Assistant Examiner* — Nicholas S Borsch
(74) *Attorney, Agent, or Firm* — Oliff PLC

(57) ABSTRACT

A handpiece for a surgical instrument having a valve position sensing circuit arranged to detect the position of a valve arranged to control the flow of fluid through the suction lumen of the instrument. The distal end of the handpiece is arranged to couple to a cutting accessory. The handpiece comprises: a housing; a suction lumen within the housing extending from the distal end of the handpiece to a proximal end of the handpiece; a valve arranged to control the flow of fluid through the suction lumen; and a valve position sensing circuit arranged to detect a position of the valve. The valve position sensing circuit can be used to alert a surgeon if the valve is closed when it would be preferable for it to be open. For example, if the motor is overheating, the in-joint temperature is too high, or the RF component is activated.

11 Claims, 6 Drawing Sheets

(52) U.S. Cl.
CPC ............... *A61B 2018/00744* (2013.01); *A61B 2018/00791* (2013.01); *A61B 2218/007* (2013.01)

(56) References Cited

U.S. PATENT DOCUMENTS

| | | | |
|---|---|---|---|
| 2003/0135151 A1 | 7/2003 | Deng | |
| 2004/0138687 A1* | 7/2004 | Himes | A61M 1/774 |
| | | | 606/167 |
| 2004/0225310 A1 | 11/2004 | Culp et al. | |
| 2006/0074405 A1 | 4/2006 | Malackowski et al. | |
| 2009/0069796 A1* | 3/2009 | Oskin | A61M 5/44 |
| | | | 604/28 |
| 2009/0270899 A1 | 10/2009 | Carusillo et al. | |
| 2014/0303611 A1* | 10/2014 | Shadduck | A61B 18/148 |
| | | | 606/33 |
| 2017/0332891 A1* | 11/2017 | Yang | A61L 2/16 |
| 2018/0008754 A1* | 1/2018 | Swift | F21V 33/0068 |
| 2018/0132850 A1 | 5/2018 | Leimbach et al. | |
| 2020/0054356 A1* | 2/2020 | Miller | A61B 17/320758 |
| 2020/0390496 A1* | 12/2020 | Houden | A61B 90/37 |

FOREIGN PATENT DOCUMENTS

| | | |
|---|---|---|
| JP | 2012-519023 A | 8/2012 |
| JP | 2015-500698 A | 1/2015 |
| JP | 2019-535447 A | 12/2019 |
| WO | 2006/036600 A1 | 4/2006 |

OTHER PUBLICATIONS

Jan. 21, 2021 Search Report issued in UK Patent Application No. GB2012025.9.

Nov. 1, 2022 Office Action issued in Japanese Patent Application No. 2021-112863.

Nov. 29, 2023 Office Action issued in British Patent Application No. GB2012025.9.

May 2, 2024 Combined Search and Examination Report issued in UK Patent Application No. 2404694.8.

May 2, 2024 Combined Search and Examination Report issued in UK Patent Application No. 2404698.9.

\* cited by examiner

FLOW VALVE POSITION SENSOR FOR AN ELECTROSURGICAL DEVICE

TECHNICAL FIELD

Embodiments of the present invention described herein relate to a surgical device, and in particular to a flow valve position sensing circuit for a surgical device.

BACKGROUND TO THE INVENTION AND PRIOR ART

Electrosurgical instruments provide advantages over traditional surgical instruments in that they can be used for coagulation and tissue sealing purposes. One such prior art arrangement is known from US 2018/0132850 A1, which describes a surgical instrument with interchangeable shaft assemblies. US 2018/0132850 A1 describes using a Hall Effect sensor and a magnet to determine whether a trigger for releasing a shaft assembly from the surgical instrument's housing is actuated or not.

Arthroscopic shavers are used in keyhole surgery to remove tissue from the surgical field. The vast majority of shavers (see FIGS. 1-3 for examples) use a mechanical flow valve situated within the handpiece to adjust the flow rate of saline out of the surgical field. The saline is sucked out through the handpiece due to a back pressure that is applied to a tube connection at the rear of the handpiece.

Currently, the flow valves in arthroscopic shavers are purely a mechanical interface, and do not provide any information with respect to the positioning of the flow valve with respect to the operation of the shaver. DC electric motors are used within arthroscopic shavers to actuate the mechanical prime mover (e.g., a mechanical shaver). Through normal operating procedures the motors produce latent heat and may require cooling. The saline flowing through the handpiece helps to remove some of the latent heat from the motor. If the motor is allowed to heat up excessively, the motor may become damaged or may heat the handpiece to an unacceptable temperature, such that it is too hot for the surgeon to hold. Additionally, it may be the case that the motor reaches a temperature where a thermal cut-out is activated and the motor needs to be left to cool for a period of time, resulting in a potential delay to the procedure. In the instance where the motor requires cooling from the saline flow, the surgeon may not be aware of this and therefore may not have the flow valve in the open position.

SUMMARY OF THE INVENTION

Embodiments of the present invention aim to provide a solution to the above identified drawbacks of the prior art by providing an improved handpiece for a surgical instrument having a sensing circuit to monitor the condition of the mechanical flow valve. This allows the condition of the valve to be electronically monitored at all times. The sensing circuit can then notify the user of the instrument if the valve is closed when ideally it should be open for any reason. For example, this reason could be to prevent extreme overheating of the motor, to cool the in-joint temperature, or to improve the RF function performance.

In view of the above, from one aspect the present invention provides a handpiece for a surgical instrument, a distal end of the handpiece arranged to couple to a cutting accessory, the handpiece comprising: a housing; a suction lumen within the housing extending from the distal end of the handpiece to a proximal end of the handpiece; a flow valve arranged to control the flow of fluid through the suction lumen; and a valve position sensing circuit arranged to detect a position of the valve.

Such an arrangement improves upon the known arrangements of the prior art by providing a sensing circuit which allows the condition of the flow valve (i.e. open, closed or partly open) to be continuously monitored electronically and communicated to a user when necessary. This is advantageous as the user can be notified on occasions where they are using the instrument with the valve closed when it would be preferable to have the valve open.

In some embodiments, the valve position sensing circuit detects whether the valve is in a first position, a second position, or an intermediate position between the first and second positions. The first position may be an open position. The second position may be a closed position. The valve position sensing circuit may be arranged to: sense when the valve is in the closed position, but according to a condition of the surgical instrument, should be in the open position; and prompt the user to open the valve.

In some embodiments, the valve is arranged to adjust a flow rate of saline out of a surgical site.

In some embodiments, the detected position of the valve is arranged to be communicated to a user of the electrosurgical instrument via a signal on the handpiece.

In some embodiments, the valve position sensing circuit comprises a Hall Effect sensor. The Hall Effect sensor may be arranged to be in a static position relative to the handpiece. The valve position sensing circuit may further comprise a magnet. The magnet may be arranged to move in conjunction with a lever arranged to operate the valve, such that the Hall Effect sensor can detect movement of the magnet.

Another aspect of the present disclosure provides a surgical instrument, comprising: a handpiece according to any of the embodiments described above, further comprising a motor within the housing arranged to actuate the cutting accessory in use; and a temperature sensor arranged to monitor a temperature of the motor; wherein the valve position sensing circuit is arranged to alert a user if the valve is closed when the temperature of the motor is over a threshold. This aspect is advantageous as the flow of saline through the handpiece can be used to remove latent heat from the motor and cool it down.

Another aspect of the present disclosure provides a surgical system, comprising: a surgical instrument comprising a handpiece according to any of the embodiments described above; and an in-joint temperature sensor arranged to monitor a temperature of saline in a patient's joint; wherein the valve position sensing circuit is arranged to alert a user if the valve is closed when the temperature of saline in a patient's joint is over a threshold. This aspect is advantageous as it helps to ensure that the saline temperature in the joint does not exceed a certain temperature. If the in-joint temperature is approaching unacceptable levels and the saline in the joint is not being exhausted because the valve is closed, the user may be prompted to open the valve to cool the joint temperature.

Another aspect of the present disclosure provides a surgical instrument, comprising: a handpiece according to any of the embodiments described above; and a cutting accessory comprising a shaft and an end effector, a proximal end of the shaft being coupled to the distal end of the handpiece, and a distal end of the shaft being coupled to the end effector; wherein the suction lumen further extends through the shaft to the end effector.

Another aspect of the present disclosure provides an electrosurgical instrument comprising: a surgical instrument according to the aspect described above, wherein the surgical instrument is an electrosurgical instrument with an RF component; wherein the valve position sensing circuit is arranged to alert a user if the valve is closed when the RF component is in use. This aspect is advantageous as it is known that RF performance is enhanced when the valve is open.

Another aspect of the present disclosure provides an electrosurgical system, comprising: an RF electrosurgical generator; a surgical instrument according to the aspect described above, wherein the surgical instrument is an electrosurgical instrument, the arrangement being such that in use the RF electrosurgical generator supplies an RF coagulation or ablation signal to the end effector; and a suction source, fluidly connected to the suction lumen.

BRIEF DESCRIPTION OF THE DRAWINGS

Embodiments of the invention will now be further described by way of example only and with reference to the accompanying drawings, wherein like reference numerals refer to like parts, and wherein.

DESCRIPTION OF THE EMBODIMENTS

Figure 1:
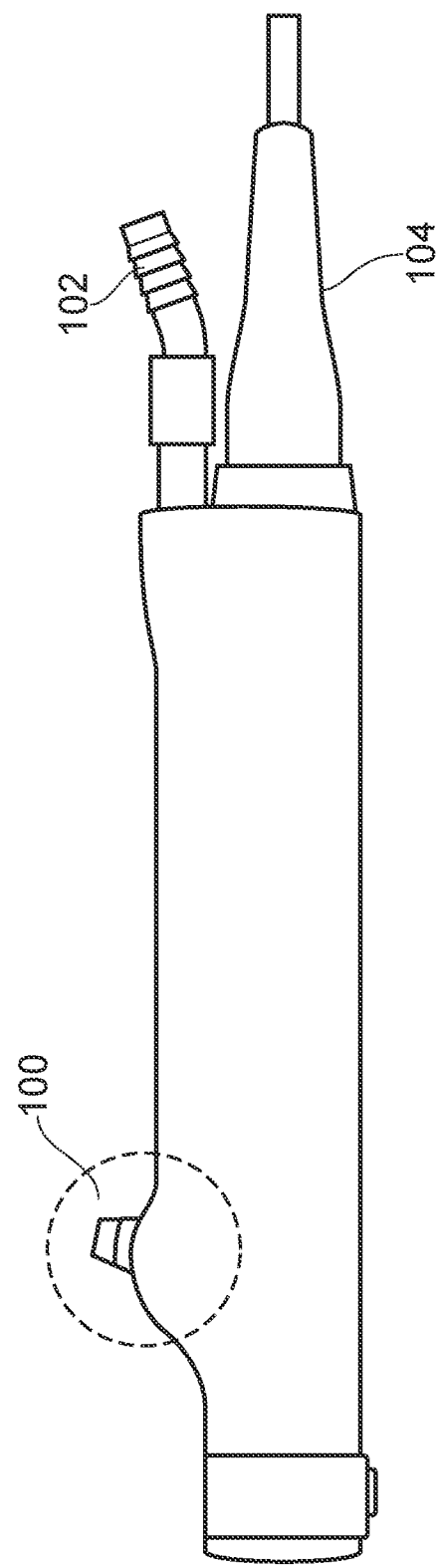
FIG. 1 is an image of a Stryker Formula Shaver Handpiece, a prior art electrosurgical instrument which has a mechanical flow valve (circled) with no way of electronically monitoring the condition of the valve.

Referring to the drawings, FIG. 1 shows a prior art arrangement, the Stryker Formula Shaver Handpiece. The mechanical valve, operated by a lever 100, does not have any way of electronically monitoring the condition of the valve. A suction tube 102 is connected to the proximal end of the handpiece, as is a power cord 104.

Figure 2:
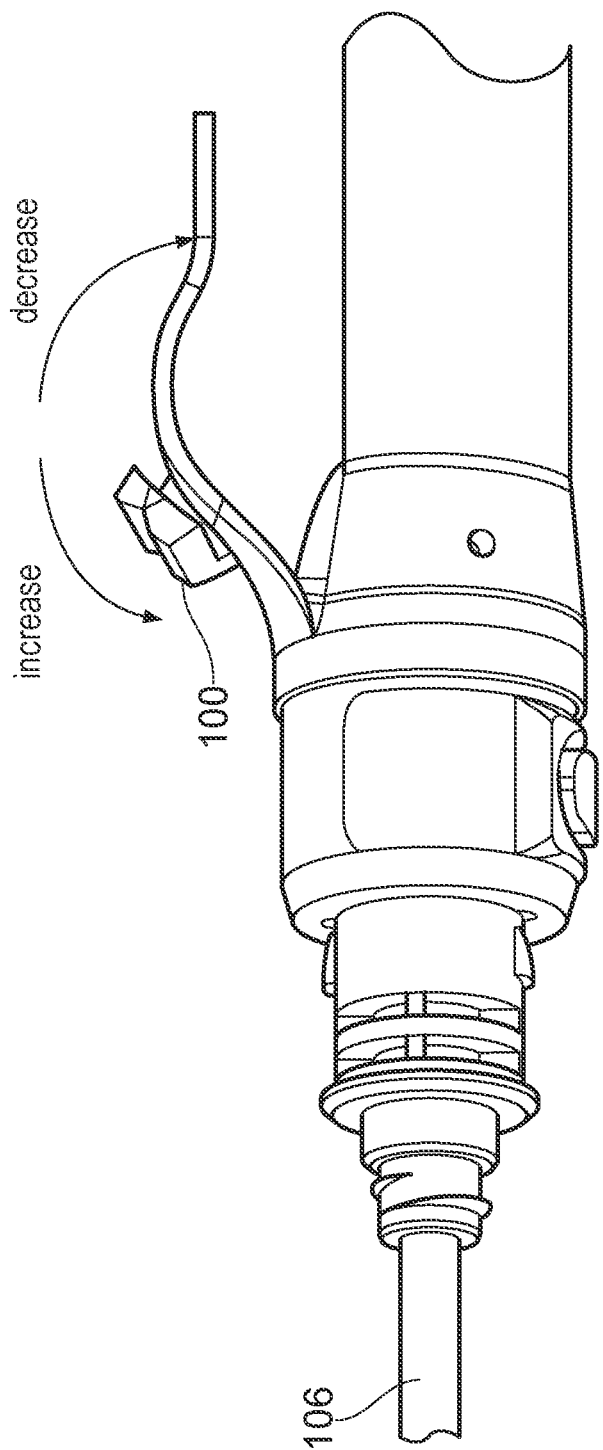
FIG. 2 is a diagram showing the Stryker Formula Shaver in more detail.

FIG. 2 shows the Stryker Formula Shaver in more detail. The mechanical valve is operated by moving the lever 100 between two positions. Increasing the flow of fluid through the valve is achieved by opening the valve, and decreasing the flow of fluid through the valve is achieved by closing the valve. At the distal end, the handpiece connects to a shaft 106, which would be connected to an end effector.

Figure 3:
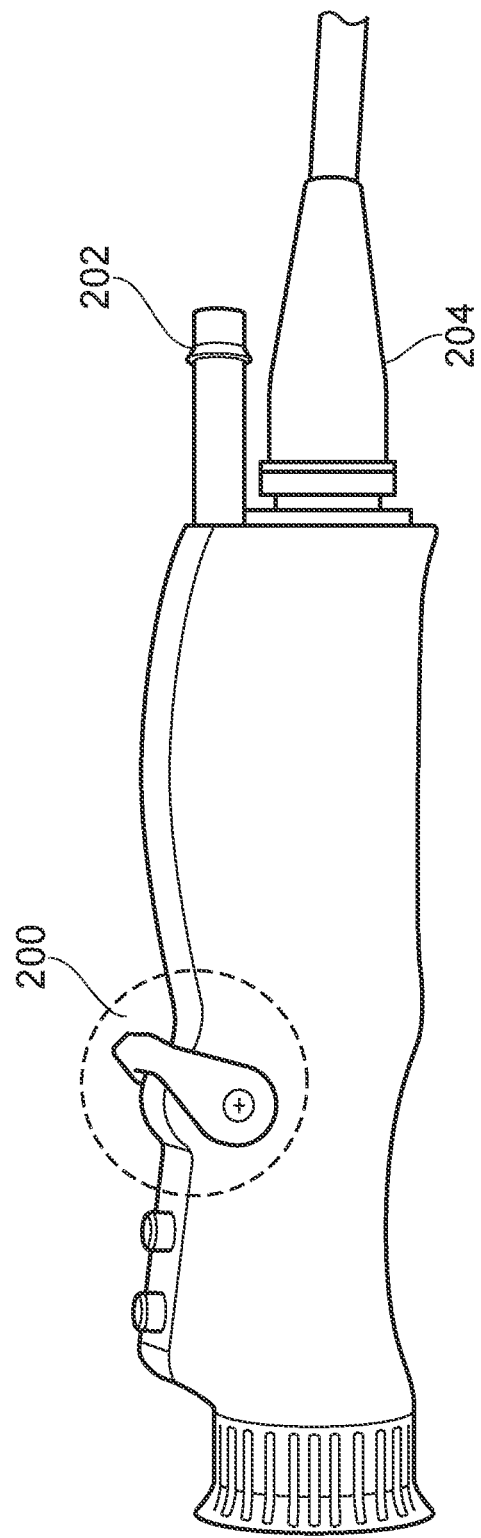
FIG. 3 is an image of a Conmed Ergo Shaver Handpiece, a prior art electrosurgical instrument which also has a mechanical flow valve (circled) with no way of electronically monitoring the condition of the valve.

FIG. 3 shows a similar prior art arrangement, the Conmed Ergo Shaver Handpiece. Again, the mechanical valve is operated by a lever 200, and there is no way of electronically monitoring the condition of the valve. A suction tube 202 is connected to the proximal end of the handpiece, as is a power cord 204.

Figure 4:
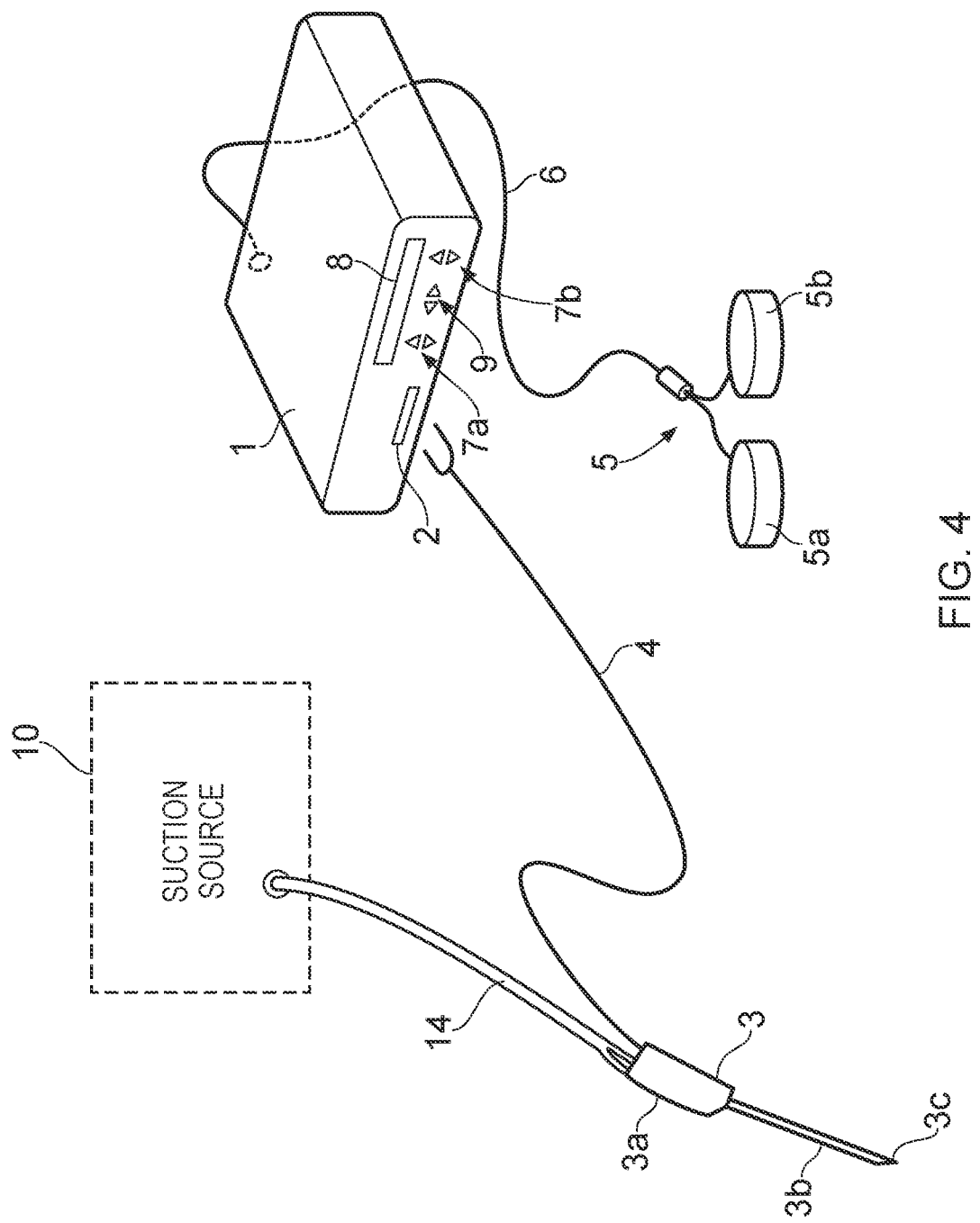
FIG. 4 is a schematic diagram of an electrosurgical system including an electrosurgical instrument.

FIG. 4 shows electrosurgical apparatus including an electrosurgical generator 1 having an output socket 2 providing a radio frequency (RF) output, via a connection cord 4, for an electrosurgical instrument 3. The instrument 3 may have irrigation and suction tubes 14 which are connected to an irrigation fluid and suction source 10. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 5a and 5b for selecting a coagulation mode or a cutting or vaporisation (ablation) mode of the generator 1 respectively. The generator front panel has push buttons 7a and 7b for respectively setting ablation (cutting) or coagulation power levels, which are indicated in a display 8. Push buttons 9 are provided as an alternative means for selection between the ablation (cutting) and coagulation modes.

The instrument 3 includes a handpiece 3a, a hollow shaft 3b extending in a distal direction away from the handpiece, and a distal end effector assembly 3c at the distal end of the shaft. A power connection cord 4 connects the instrument to the RF generator 1. The instrument may further be provided with activation buttons (not shown), to allow the surgeon operator to activate either the mechanical cutting function of the end effector, or the electrosurgical functions of the end effector, which typically comprise coagulation or ablation.

Figure 5:
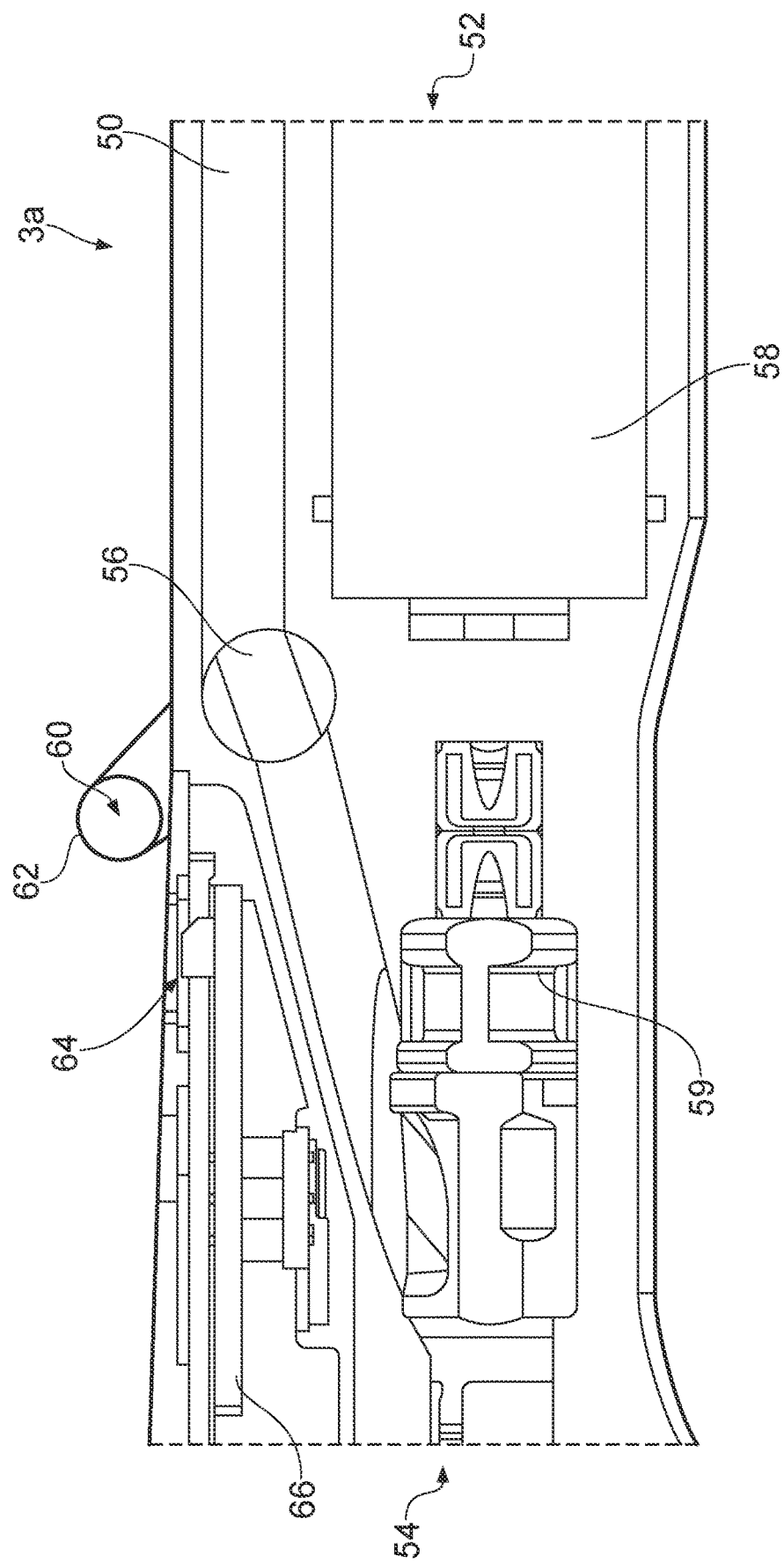
FIG. 5 is a diagram showing a flow valve in accordance with the present invention in an open position.
Figure 6:
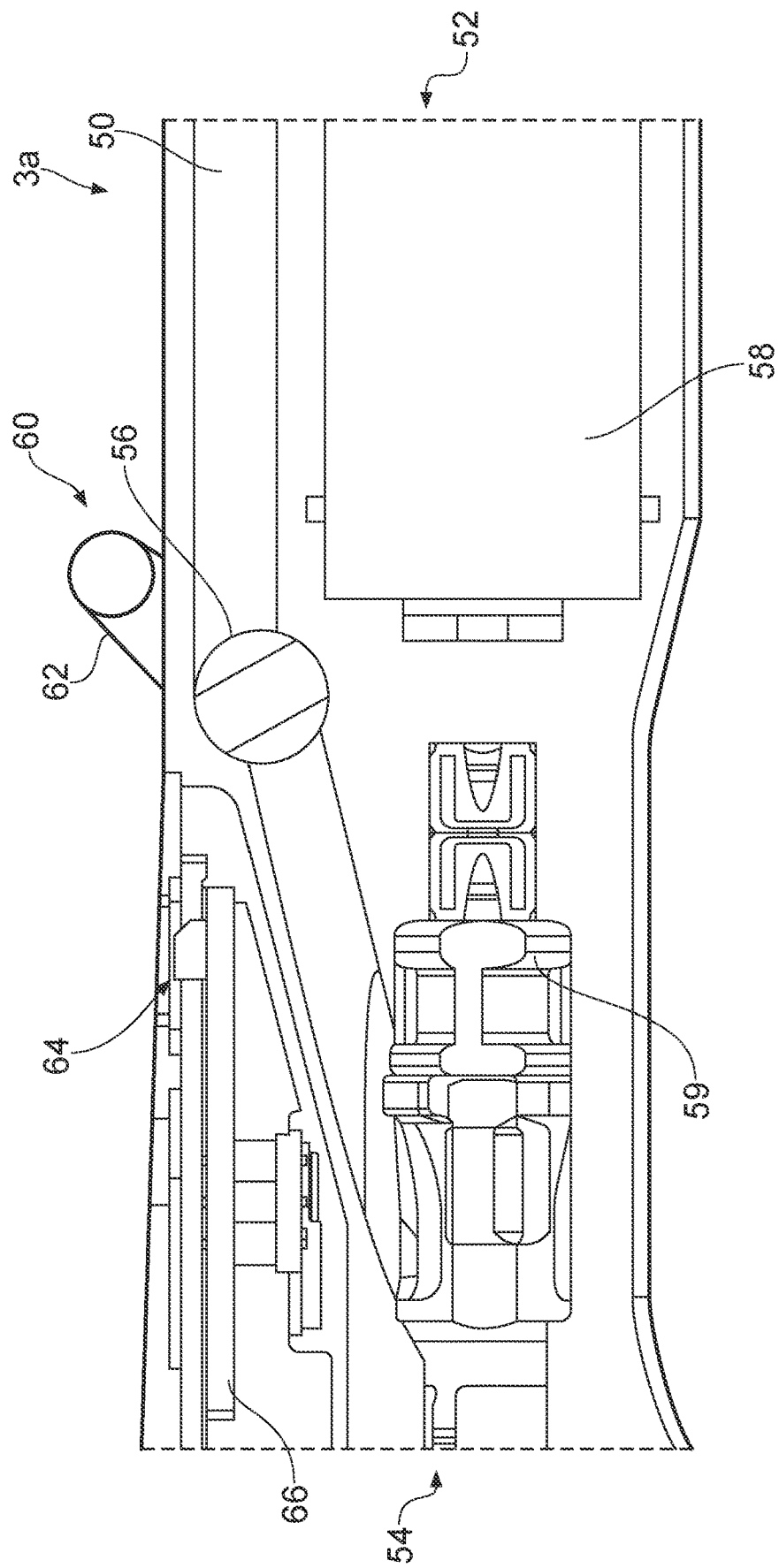
FIG. 6 is a diagram showing a flow valve in accordance with the present invention in a closed position.

FIGS. 5 and 6 show the handpiece 3a in more detail. A suction lumen 50 extends through the handpiece 3a from the proximal end of the handpiece 52 to the distal end 54. At the proximal end of the handpiece 52, the suction lumen 50 connects to a further suction tube 14 (not shown in FIGS. 5 and 6) which is connected to the suction source 10 (not shown in FIGS. 5 and 6). At the distal end of the handpiece 54, the suction lumen 50 extends through the shaft 3b (not shown in FIGS. 5 and 6) to the end effector 3c (not shown in FIGS. 5 and 6). In a surgical procedure, irrigation fluid is introduced into the surgical site in order to serve as a transport medium for removing debris from the site. The irrigation fluid containing the debris is then sucked up through the suction lumen 50. The suction force is provided by the suction source 10. A valve 56 is provided to control the flow of fluid through the suction lumen 50. FIGS. 5 and 6 show a motor 58 which is connected to the generator 1 by the power cord 4 (not shown in FIGS. 5 and 6) attached to the proximal end of the handpiece 52. The motor 58 is used to provide power to a mechanical component in the end effector, for example, a mechanical shaver component. The motor 58 may be a DC electric motor. The motor 58 is operably connected to a clutch-type arrangement 59 which allows the motor 58 to actuate the mechanical component. The clutch-type arrangement 59 allows the mechanical component to engage and disengage from the motor 58.

FIGS. 5 and 6 illustrate one method of achieving the sensing circuit of the present invention, to have a magnet 60 connected to the flow valve lever 62 and a Hall Effect sensor 64 mounted in a static position on a circuit board 66 in the handpiece 3a. The circuit board 66 acts as a processor for the sensing circuit. The magnet 60 may be any magnetic element, for example, a permanent magnet. FIG. 5 illustrates the system when the flow valve 56 is in the open position. FIG. 6 illustrates the system when the flow valve 56 is in the closed position. The Hall Effect sensor 64 can detect any relative movement of the magnet 60 by detecting changes in a magnetic field surrounding the Hall Effect sensor 64, and consequently movement of the flow valve lever 62. This enables the position of the flow valve lever 62, and consequently the position of the flow valve 56 (i.e. whether the flow valve 56 is open or closed, or somewhere in between), to be monitored. In FIG. 5, the magnet 60 (and the lever 62) is in a first position and the valve 56 is consequently open. In FIG. 6, the magnet 60 (and the lever 62) has moved to a second position, and the valve 56 is consequently closed. The movement of the magnet 60 between these two positions is detectable by the Hall Effect sensor 64, which detects the relative movement of the magnet 60 via the change in magnetic field around the Hall Effect sensor 64. The Hall Effect sensor 64 sends a signal to the processor 66 to communicate the change in position. Based on this signal, the processor 66 can determine whether the valve 56 is open or closed. The condition of the valve 56 can then be communicated to a user of the instrument via a further signal on the handpiece 3a, or via the generator 1. For example, in the context of a RF shaver instrument, if the user is using the RF part of the instrument with the flow valve 56 closed, the handpiece 3b may provide tactile feedback to warn the user. Alternatively or additionally, the generator display 8 may display a warning to the user. This is desirable as it is known that the RF performance is enhanced when the flow valve 56 is open.

The sensing circuit may also be used to alert the user to open the flow valve 56 in the event that the motor 58 in the handpiece 3b is overheating and the flow valve 56 is closed. The flow of saline through the instrument can help to remove latent heat from the motor 58.

The sensing circuit may be used in conjunction with an in-joint temperature sensor to ensure that the saline temperature in the joint is not allowed to exceed a certain point. If the in-joint temperature is approaching unacceptable levels and the saline in the joint is not being exhausted because the flow valve 56 is closed, the user could be prompted to open the flow valve 56. The hot saline would then be removed from the surgical site, allowing cooling of the joint.

In various embodiments, any number of magnetic sensing elements 60 may be used to monitor the condition of the flow valve 56. Technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

An example of an alternative to the magnet 60 and Hall Effect sensor 64 sensing circuit would be to use an accelerometer to monitor the movement of the flow valve lever.

The concepts of the present invention can be used on a wider suite of arthroscopic instruments as further embodiments, and they are not limited specifically to shaver instruments. In further embodiments the magnet may be included in the movable part of the flow control of many arthroscopic instruments.

Various modifications whether by way of addition, deletion, or substitution of features may be made to above described embodiment to provide further embodiments, any and all of which are intended to be encompassed by the appended claims.

The invention claimed is:

1. A handpiece for a surgical instrument, a distal end of the handpiece arranged to couple to a surgical end effector, the handpiece comprising:
   a housing;
   a suction lumen within the housing extending from the distal end of the handpiece to a proximal end of the handpiece;
   a flow valve arranged to control a flow of fluid through the suction lumen; and
   a flow valve position sensing circuit arranged to detect a position of the flow valve, wherein the flow valve position sensing circuit is arranged to detect whether the flow valve is in an open position or a closed position, and the flow valve position sensing circuit is further arranged in use to:
      sense when the flow valve is in the closed position but, based on a condition of the surgical instrument during surgery on a surgical site, sense whether the flow valve should be in the open position, the condition including an excessive temperature of the handpiece or the surgical site as measured by a temperature sensor; and
      when the flow valve is sensed to be in the closed position, but based on according to a condition of the surgical instrument during surgery at the surgical site, should be in the open position, output a signal arranged to prompt a user to open the flow valve to increase a flow rate of saline from the surgical site to cool both the surgical site and the handpiece.

2. The handpiece according to claim 1, wherein the flow valve position sensing circuit is arranged to detect whether the flow valve is in an intermediate position between the open and closed positions.

3. The handpiece according to claim 1, wherein the detected position of the flow valve is arranged to be communicated to the user of the surgical instrument via a signal on the handpiece.

4. The handpiece according to claim 3, wherein the signal on the handpiece is a tactile feedback signal.

5. The handpiece according to claim 1, wherein the flow valve position sensing circuit comprises:
   a magnet mounted on a user-operable lever configured to move between a first position corresponding to the open position of the flow valve and a second position corresponding to the closed position of the flow valve; and
   a Hall Effect sensor arranged in use to detect movement of the magnet as the user-operable lever is moved by a user.

6. The handpiece according to claim 5, wherein the Hall Effect sensor is arranged to be in a static position relative to the handpiece.

7. A surgical instrument, comprising:
   a handpiece according to claim 1, further comprising a motor within the housing arranged to actuate a cutting accessory in use; and
   a temperature sensor arranged to monitor a temperature of the motor;
   wherein the flow valve position sensing circuit is arranged to alert a user if the flow valve is closed when the temperature of the motor is over a threshold.

8. A surgical system, comprising:
   a surgical instrument comprising a handpiece according to claim 1; and
   an in-joint temperature sensor arranged to monitor a temperature of saline in a patient's joint;
   wherein the flow valve position sensing circuit is arranged to alert a user if the flow valve is closed when the temperature of saline in a patient's joint is over a threshold.

9. A surgical instrument, comprising:
   a handpiece according to claim 1; and
   a cutting accessory comprising a shaft and an end effector, a proximal end of the shaft being coupled to the distal end of the handpiece, and a distal end of the shaft being coupled to the end effector;

wherein the suction lumen further extends through the shaft to the end effector.

10. An electrosurgical instrument, comprising:
a surgical instrument according to claim 9, wherein the surgical instrument is an electrosurgical instrument with an RF component;
wherein the flow valve position sensing circuit is arranged to alert a user if the valve is closed when the RF component is in use.

11. An electrosurgical system, comprising:
an RF electrosurgical generator;
a surgical instrument according to claim 9, wherein the surgical instrument is an electrosurgical instrument, the arrangement being such that in use the RF electrosurgical generator supplies an RF coagulation or ablation signal to the end effector; and
a suction source, fluidly connected to the suction lumen.

* * * * *